(12) United States Patent
Azeredo Da Silveira Lajaunias et al.

(10) Patent No.: US 12,059,496 B2
(45) Date of Patent: Aug. 13, 2024

(54) TREATMENT OF PNEUMONIA

(71) Applicant: COMBIOXIN SA, Geneva (CH)

(72) Inventors: Samareh Azeredo Da Silveira Lajaunias, Geneva (CH); Frédéric Lajaunias, Geneva (CH)

(73) Assignee: COMBIOXIN SA, Geneva (CH)

( * ) Notice: Subject to any disclaimer, the term of this patent is extended or adjusted under 35 U.S.C. 154(b) by 0 days.

(21) Appl. No.: 17/047,666

(22) PCT Filed: Apr. 16, 2019

(86) PCT No.: PCT/EP2019/059826
§ 371 (c)(1),
(2) Date: Oct. 14, 2020

(87) PCT Pub. No.: WO2019/201937
PCT Pub. Date: Oct. 24, 2019

(65) Prior Publication Data
US 2021/0030677 A1 Feb. 4, 2021

(30) Foreign Application Priority Data
Apr. 17, 2018 (EP) .................... 18167848

(51) Int. Cl.
*A61K 9/127* (2006.01)
*A61K 9/00* (2006.01)
*A61K 31/575* (2006.01)
*A61K 31/688* (2006.01)
*A61P 11/00* (2006.01)

(52) U.S. Cl.
CPC ............ *A61K 9/127* (2013.01); *A61K 9/0019* (2013.01); *A61K 31/575* (2013.01); *A61K 31/688* (2013.01); *A61P 11/00* (2018.01)

(58) Field of Classification Search
None
See application file for complete search history.

(56) References Cited

FOREIGN PATENT DOCUMENTS

WO WO 2013/186286 A1 12/2013
WO WO-2013186286 A1 * 12/2013 ........... A61K 9/1271

OTHER PUBLICATIONS

ClinicalTrials.gov (https://clinicaltrials.gov/ct2/show/NCT02583373 (Year: 2015).*
Torres et al (Am J Respir Med, 2003, 2(1), 39-54) (Year: 2003).*
International Search Report issued Jul. 8, 2019, in International Appl. No. PCT/EP2019/059826.
B. Francois, "Adjunctive intravenous anti-toxin treatment with CAL02 in severe acute community-acquired pneumonia due to Streptococcus pneumonia. A first-in-man, multicentre, double-blind, placebocontrolled study," Intensive Care Medicine Experimental 6(Suppl 2):0995 (2018).

(Continued)

*Primary Examiner* — Gollamudi S Kishore
(74) *Attorney, Agent, or Firm* — BakerHostetler (57) ABSTRACT

The present invention relates to a composition comprising a mixture of empty liposomes, wherein said mixture of empty liposomes comprises (a) a first empty liposome comprising cholesterol, wherein the amount of cholesterol is at least 30% (weight per weight); and (b) a second empty liposome comprising sphingomyelin, for use in adjunctive treatment of 5 pneumonia in a human patient.

21 Claims, 4 Drawing Sheets

(56) References Cited

OTHER PUBLICATIONS

B. Francois, "Cal02: A liposomal anti-toxin therapy in infections—a new adjunctive therapeutic approach for severe community-acquired pneumonia," Database Embase Elsevier Science Publishers, Amsterdam, NL (Mar. 1, 2017).

B.D. Henry et al., "Engineered liposomes sequester bacterial exotoxins and protect from severe invasive infections in mice," Nature Biotechnology 33(1):81-88 (2014).

S. Azeredo Da Silveira et al., "Liposomes as novel anti-infectives targeting bacterial virulence factors?", Expert Review of Anti-Infective Therapy 13(5): 531-533 (2015).

P.-F. Laterre et al., "CAL02, a novel antitoxin liposomal agent, in severe pneumococcal pneumonia: a first-in-human, double-blind, placebo-controlled, randomized trial," Lancet Infect Dis 19:620-630 (May 2, 2019).

* cited by examiner

TREATMENT OF PNEUMONIA

The present invention relates to a composition comprising a mixture of empty liposomes, wherein said mixture of empty liposomes comprises (a) a first empty liposome comprising cholesterol, wherein the amount of cholesterol is at least 30% (weight per weight); and (b) a second empty liposome comprising sphingomyelin, for use in adjunctive treatment of pneumonia in a human patient.

RELATED ART

Today's most challenging issues for pneumonia and severe pneumonia are the threatening rise of resistant strains and the unacceptably high rates of treatment failure and mortality despite best of care. Antimicrobial resistance poses a global threat to health care and economics and new therapeutic strategies to overcome drug resistance and alternatives to antibiotics are urgently needed (O'Neill, J., *Review on Antimicrobial Resistance* (2014); Bush, K. et al. *Nature reviews. Microbiology* 9, 894-896 (2011)). A retrospective overview of the performance of new antibiotics has revealed their inability to significantly improve cure rates and/or decrease mortality rates on their own (Azeredo da Silveira, S. and Perez, A. *Expert Rev Anti Infect Ther* 15, 973-975 (2017)).

Intensive-care unit (ICU) patients with pneumonia still have a bleak prognosis or may suffer from long-term and difficult-to-treat consequences. By way of examples with *Streptococcus pneumoniae*, *Staphylococcus aureus* and *Pseudomonas aeruginosa*, which are among the most common causing pathogens: Mortality rates in adult ICU patients suffering from a severe pneumococcal pneumonia can still reach 40% despite best of care and appropriate antibiotherapy (Welte, T., et al., *Thorax* 67, 71-79 (2012); Torres, A. *Community Acquired Infection* 1, 1 (2017)). *Streptococcus pneumoniae* is the most frequently identified pathogen of community-acquired bacterial pneumonia and its severe forms are associated with high morbidity and mortality (Blasi, F., et al. *Clinical microbiology and infection: The official publication of the European Society of Clinical Microbiology and Infectious Diseases* 18 Suppl 5, 7-14 (2012). Despite preventive measures, such as pneumococcal vaccines, and current medical treatment (mostly antibiotic therapy, alone or in combination), there is a clear unmet medical need for additional treatment options (Vernatter, J. and Pirofski, L. A., *Current opinion in infectious diseases* 26, 277-283 (2013); Lucas, R. et al. *Toxins* 5, 1244-1260 (2013)). *Staphylococcus aureus* bacteraemia has persistently been associated with a 30-day mortality rate of 20% since the 1990s (Van Hal, S. J. et al., *Clinical microbiology reviews* 25, 362-386 (2012)), and mortality rates in ICU patients infected with methicillin-resistant *Staphylococcus aureus* (MRSA) are 50% higher than that expected with methicillin-sensitive *Staphylococcus aureus* (MSSA) infection (Hanberger, H. et al., *International journal of antimicrobial agents* 38, 331-335 (2011)). Mortality due to multi-drug resistant *Pseudomonas aeruginosa*, which has become one of the most frequent causative agents of nosocomial infections and ventilators-associated pneumonia, and which is the major cause of morbidity in patients with cystic fibrosis or chronic obstructive pulmonary disease, exceeds 35% (Ramirez-Estrada, S., et al. *Infect Drug Resist* 9, 7-18 (2016)).

Other bacteria may also cause respiratory infectious disease and produce virulence factors that cause the disease to become severe and with complications, such as *Haemophilus influenzae*, *Klebsiella pneumoniae*, *Escherichia coli*, *Acinetobacter baumanii*, *Bordetella pertussis*, *Moraxella catarrhalis*, or *Mycobacterium tuberculosis*.

Bacteria virulence factors promote colonization and growth in the host, they disrupt tissue barriers, they facilitate tissue penetration and bacterial dissemination, and they hinder the host's immune defence against the pathogen (Los, F. C., et al. *MMBR* 77, 173-207 (2013)). The pro-inflammatory and anti-inflammatory cascades resulting from the release of bacterial toxins lead patients to deadly complications.

In spite of best available therapy, many patients die from complications of severe pneumonia, which may occur days after starting antibiotics, when tissues are already pathogen-free and the pulmonary process is clearing. When patients suffering from pneumonia are admitted to the hospital, infection has been developing for several days, bacterial loads are at a peak and toxins are massively released. For instance, *Streptococcus pneumoniae*'s toxin pneumolysin, which is not secreted into the extracellular medium but is released by bacterial autolysis or lysis due to antibiotics, is therefore massively released following bacterial lysis caused by antibiotics (Lucas, R. et al. *Toxins* 5, 1244-1260 (2013); Baumgartner, D. et al., *BMC microbiology* 16, 154 (2016); Hirst, R. A., et al., *Clin Exp Immunol* 138, 195-201 (2004)). Of note, pneumolysin promotes disease progression, pneumococcal replication and the development of invasive disease, and plays a key role in severe and fatal complications. In fact, the pathogenic impact of pneumolysin is multifactorial (Lucas, R. et al. *Toxins* 5, 1244-1260 (2013); Kadioglu, A., et al., *Nature reviews. Microbiology* 6, 288-301 (2008)). More specifically, pneumolysin causes widespread direct cellular lysis and tissue damage. It affects the alveolar-capillary barrier of the lung, thus contributing to pulmonary alveolar oedema and haemorrhage, which stimulate intra-alveolar bacterial multiplication and favours invasiveness of the pathogen by facilitating pneumococcal penetration into the pulmonary interstitium and into the bloodstream. Pneumolysin also alters the balance of local and systemic immune responses by triggering pro-inflammatory reactions, by exerting direct inhibitory effects on immune cells and by blocking the complement; it impedes the initiation of host immune responses during the first hours of infection and the effective action of the first line of immune defence against the bacteria. Pneumolysin thereby also plays an essential role in the immunomodulatory side effects of antibiotic therapies and the systemic inflammatory response and clinical aggravation, following the massive release of toxins correlating with the bacteriolytic effects of antibiotics. Toxin-mediated complications may arise, possibly including respiratory failure, empyema, meningitis, arthritis, endocarditis, acute coronary syndromes, heart failure, osteomyelitis, deafness, epilepsy, hydrocephalus, cognitive deficits.

Tailored empty liposomes such as empty liposomes composed of cholesterol and/or sphingomyelin and their use for the treatment of bacterial infections have recently been described to serve as traps for virulence factors such as bacterial toxins, enzymes and virulent appendages (WO 2013/186286; Henry B D et al., Nat Biotechnol 2015; 33(1):81-88; Azeredo da Silveira, S and Perez, A, Expert Rev. Anti Infect. Ther. 2015; 13(5):531-533).

SUMMARY OF THE INVENTION

The preferred composition of the present invention showed surprisingly positive results in a first-in-man study for the treatment of pneumonia. Not only has been shown that said preferred composition of the present invention is safe and well tolerated at all dose levels tested, but furthermore consistent and promising efficacy data were obtained across different clinical parameters. Based on this promising efficacy data and its believed mechanism of action, efficacy in a envisaged second study with hospitalized patients suffering from a suspected or confirmed infection and presenting signs of development of complications or severity, notably suffering from a community-acquired pneumonia, hospital-acquired pneumonia, ventilation-associated pneumonia, intra-abdominal infections, skin and soft tissue infections, urinary tract infections, or bacteraemia is therefore plausible.

The first study compared the preferred composition of the present invention plus standard antibiotic therapy with placebo plus standard antibiotic therapy in adult patients admitted to intensive care units (ICUs) due to severe community-acquired pneumococcal pneumonia. Two different doses of the preferred composition of the present invention were compared, namely a low dose (4 mg/kg—Low-Dose) and a high does (16 mg/kg—High-Dose). The results showed a synergistic effect of the preferred composition of the present invention (named CAL02) with antibiotic treatment.

As a consequence, it has been shown that the preferred compositions of the present invention, thus, capture and neutralize toxins released from a wide range of bacteria associated with severe infections in a synergistic manner with antibiotic treatment in human patients. It is these toxins which are responsible for the development of severe and fatal complications. The preferred compositions of the present invention are, thus, first-in-class non-antibiotic liposomal drugs which are active against both Gram-positive and Gram-negative bacteria, including those which are multi-drug resistant. The preferred inventive compositions act regardless of the resistance profile of the target pathogen and does not elicit the emergence of resistance.

Thus, in a first aspect, the present invention provides for a composition comprising, preferably consisting of, a mixture of empty liposomes, wherein said mixture of empty liposomes comprises, preferably consists of, (a) a first empty liposome comprising cholesterol, wherein the amount of cholesterol is at least 30% (weight per weight); and (b) a second empty liposome comprising sphingomyelin; for use in adjunctive treatment of pneumonia in a human patient, wherein preferably said pneumonia is selected from a Community Acquired Pneumonia (CAP), a Hospitalization Acquired Pneumonia (HAP) and a Ventilator-associated pneumonia (VAP).

In a further preferred embodiment, said pneumonia is a severe pneumonia, wherein preferably said severe pneumonia is selected from a severe Community Acquired Pneumonia (sCAP), and wherein again further preferably said severe pneumonia is severe Community Acquired Pneumococcal Pneumonia (sCAPP) in a human patient.

Further aspects and embodiments of the present invention will become apparent as this description continues.

DESCRIPTION OF FIGURES

FIG. 1: Evolution of the severity scores SOFA (FIG. 1A) and APACHE II (FIG. 1B), from baseline (pre-dose) to Day 8 in the Placebo (diamonds), CAL02 Low Dose (triangles) and CAL02 High Dose (squares) groups. *p<0.05, **p<0.005

FIG. 2: Evolution of pharmacodynamics biomarkers: C-reactive protein (CRP) (FIG. 2A), Procalcitonin (PCT) (FIG. 2B), and Interleukin-6 (FIG. 2C), from baseline (pre-dose) to Day 8 in the Placebo (diamonds), CAL02 Low Dose (triangles) and CAL02 High Dose (squares) groups.

FIG. 3: Time to ICU discharge (FIG. 3A), p<0.05, and time to hospital discharge (FIG. 3B) in the Placebo (diamonds) and CAL02 High Dose (squares) groups.

DETAILED DESCRIPTION OF THE INVENTION

Unless defined otherwise, all technical and scientific terms used herein have the same meanings as commonly understood by one of ordinary skill in the art to which this invention belongs.

The term "about", as used herein shall have the meaning of +/−5%. For example about 50% shall mean 47.5% to 52.5%. Preferably, the term "about", as used herein shall have the meaning of +/−3%. For example about 50% shall mean 48.5% to 51.5%.

When the terms "a," or "an" are used herein, they mean "at least one" unless indicated otherwise. In particular, the use of the terms "a," or "an" in association with said single empty liposome, said first empty liposome and said second empty liposome to describe the empty liposomes and mixtures of empty liposomes in accordance with the present invention should typically and preferably refer to single empty liposomes and mixtures of empty liposomes comprising said first empty liposomes and said second empty liposomes.

All ranges of values disclosed herein, should refer to all values falling within said range including the values defining the range. By way of clarification, for example, a value of 12 to 13 should refer to a value of 12 or 13 or all values falling within 12 and 13.

The term "empty liposome" as used herein, refers to liposomes, preferably artificial liposomes, having a mean diameter of 20 nm to 10 μm, preferably of 20 to 500 nm, and further preferably having a mean diameter of 20 nm to 400 nm, again further preferably of 40 nm to 400 nm or 20 nm to 200 nm, and consist of one or more phospholipid bilayers, and are typically and preferably unilamellar vesicles and multilamellar vesicles, more preferably small unilamellar vesicles (SUVs). In a preferred embodiment, the term "empty liposome" as used herein, typically and preferably refers to liposomes not incorporating any drug, typically and preferably to liposomes not incorporating any pharmaceutical drug. "Incorporated/Incorporating" as used herein and when referring to the inventive empty liposomes, typically and preferably, means encapsulated/encapsulating into the cavity of the liposome, within the potential double layer of the liposome, or as part of the membrane layer of the liposome. In another preferred embodiment, the term "empty liposome" as used herein, typically and preferably refers to liposomes consisting of sphingomyelin and cholesterol or consisting of sphingomyelin in accordance with the present invention and solely further comprises water-soluble inorganic compounds and/or water-soluble organic molecules, wherein typically and preferably said water-soluble inorganic compounds and/or water-soluble organic molecules derive from the synthesis of said inventive empty liposomes, and wherein typically and preferably, said water-soluble inorganic compounds are inorganic salts preferably selected from NaCl, KCl, $MgCl_2$, and wherein said water-soluble organic molecules are buffering agents, wherein preferably said water-soluble organic molecules are selected from glucose and HEPES. Typically and preferably, said water-soluble inorganic compounds and/or water-soluble organic molecules are incorporated in the inventive empty liposomes of the present invention due to their presence during the production of the inventive empty liposomes. In another preferred embodiment, the term "empty liposome" as used herein, typically and preferably refers to liposomes consisting of sphingomyelin and cholesterol or consisting of sphingomyelin in accordance with the present invention and wherein said empty liposomes do not comprise an antioxidant. In a further preferred embodiment, the term "empty liposome" as used herein, typically and preferably refers to liposomes consisting of sphingomyelin and cholesterol or consisting of sphingomyelin in accordance with the present invention and solely further comprises water-soluble inorganic compounds and/or water-soluble organic molecules, wherein typically and preferably said water-soluble inorganic compounds and/or water-soluble organic molecules derive from the synthesis of said inventive empty liposomes, and wherein typically and preferably, said water-soluble inorganic compounds are inorganic salts preferably selected from NaCl, KCl, $MgCl_2$, and wherein said water-soluble organic molecules are buffering agents, wherein preferably said water-soluble organic molecules are selected from glucose and HEPES, and wherein said empty liposomes consisting of sphingomyelin and cholesterol or consisting of sphingomyelin in accordance with the present invention do not comprise an antioxidant.

The term "treating", "treatment" or "therapy" as used herein refers to means of obtaining a desired physiological effect. The effect may be therapeutic in terms of partially or completely curing a disease or a condition and/or symptoms attributed to the disease or the condition. The term refers to inhibiting the disease or condition, i.e. arresting its development; or ameliorating the disease or condition, i.e. causing regression of the disease or condition.

As used herein, the term "for use" as used in "composition for use in treatment of a disease" shall disclose also the corresponding method of treatment and the corresponding use of a preparation for the manufacture of a medicament for the treatment of a disease".

The term "pneumonia" as used herein should encompass "Community Acquired Pneumonia" (CAP), "Hospital Acquired Pneumonia" (HAP) or "Ventilator-associated pneumonia" (VAP).

The term "Community Acquired Pneumonia" or "CAP" is known to the person skilled in the art, see e.g. the IDSA/ATS Guidelines for CAP in Adults (CID 2007:44 (Suppl 2) S27). In particular, the term refers to pneumonia acquired outside the hospital.

The term "Hospital Acquired Pneumonia (HAP)" refers to pneumonia acquired during or after hospitalization for another illness or procedure with onset at least 48 to 72 hours after admission.

As defined herewith, "ventilator associated pneumonia (VAP)" is a pneumonia that develops 48 hours or longer after mechanical ventilation and that is characterized by an invasion of the lower respiratory tract and lung parenchyma by microorganisms. VAP is a potentially serious medical condition.

Pneumonia is caused by infection with a broad range of microorganisms including bacteria such as *Streptococcus pneumoniae, Haemophilus influenzae, Legionella pneumophilia, Staphylococcus aureus* and *Pseudomonas aeruginosa* for CAP and gram-negative bacilli such as *Pseudomonas aeruginosa* and *Serratia marcescens*, as well as *Staphylococcus aureus, Klebsiella pneumoniae, Escherichia coli, Stenotrophomonas maltophilia, Acinetobacter species*, and *Haemophilus influenzae* for HAP (cf. Cilloniz et al., Thorax. 2011 April; 66(4):340-6 and Jones R N. Clin Infect Dis 2010 August; 51(Suppl1):S81-7).

The term "severe Community Acquired Pneumonia" or "sCAP" is known to the skilled person. In particular, the term "severe Community Acquired Pneumonia" or "sCAP" refers to the subgroup of Community Acquired Pneumonia patients that require intensive care. The Infectious Disease Society of America (IDSA) and the American Thoracic Society (ATS) have issued guidelines on the management of CAP including a definition of sCAP (cf. Mandell et al., 2007, Infectious Diseases Society of America/American Thoracic Society Consensus Guidelines on the Management of Community-Acquired Pneumonia in Adults, Clin. Inf. Dis. 2007: 44:S27-72 (Suppl 2), Table 4). According to the IDSA/ATS guidelines sCAP is defined as CAP requiring intensive care. Admission to the intensive care unit is recommended if the CAP patient shows one or both of two major criteria, or presence of three minor criteria from the list as described in Example 1 and as effected in the presented study.

Thus, in first aspect, the present invention provides for a composition comprising, preferably consisting of, a mixture of empty liposomes, wherein said mixture of empty liposomes comprises, preferably consists of, (a) a first empty liposome comprising cholesterol, wherein the amount of cholesterol is at least 30% (weight per weight); and (b) a second empty liposome comprising sphingomyelin; for use in adjunctive treatment of pneumonia in a human patient, wherein preferably said pneumonia is selected from a Community Acquired Pneumonia (CAP), a Hospitalization Acquired Pneumonia (HAP) and a Ventilator-associated pneumonia (VAP), wherein further preferably said pneumonia is Community Acquired Pneumonia (CAP), and wherein again further preferably said pneumonia is Community Acquired Pneumococcal Pneumonia (CAPP) in a human patient.

In another aspect, the present invention provides for a composition comprising, preferably consisting of, a mixture of empty liposomes, wherein said mixture of empty liposomes comprises, preferably consists of, (a) a first empty liposome comprising cholesterol, wherein the amount of cholesterol is at least 30% (weight per weight); and (b) a second empty liposome comprising sphingomyelin; for use in adjunctive treatment of pneumonia in a human patient, wherein preferably said pneumonia is a severe pneumonia, wherein preferably said severe pneumonia is selected from a severe Community Acquired Pneumonia (sCAP), a Hospitalization Acquired Pneumonia (HAP) and a Ventilator-associated pneumonia (VAP), wherein further preferably said severe pneumonia is a severe Community Acquired Pneumonia (sCAP), and wherein again further preferably said severe pneumonia is severe Community Acquired Pneumococcal Pneumonia (sCAPP) in a human patient.

In a preferred embodiment, said second empty liposome (b) comprises said sphingomyelin as sole lipid component.

In a preferred embodiment, said second empty liposome (b) consists of sphingomyelin.

In a preferred embodiment, the amount of cholesterol of said first empty liposome (a) is 30%-70% (weight per weight), and wherein preferably the amount of cholesterol of said first empty liposome (a) is 35%-60% (weight per weight).

In a preferred embodiment, the amount of cholesterol of said empty liposome (a) is 45%-55% (weight per weight), and wherein preferably the amount of cholesterol of said empty liposome (a) is about 50% (weight per weight).

In a preferred embodiment, said first empty liposome (a) consists of cholesterol and sphingomyelin, and wherein preferably the amount of cholesterol of said empty liposome (a) is 45%-55% (weight per weight), and wherein further preferably the amount of cholesterol of said empty liposome (a) is about 50% (weight per weight).

In a preferred embodiment, said first empty liposome (a) comprises said cholesterol and said sphingomyelin as sole lipid components.

In a preferred embodiment, the amount of cholesterol of said empty liposome (a) is 45%-55% (weight per weight), and wherein preferably the amount of cholesterol of said empty liposome (a) is about 50% (weight per weight), and wherein said second empty liposome (b) consists of sphingomyelin.

In a preferred embodiment, said first empty liposome (a) consists of cholesterol and sphingomyelin, and wherein the amount of cholesterol of said empty liposome (a) is 45%-55% (weight per weight), and wherein preferably the amount of cholesterol of said empty liposome (a) is about 50% (weight per weight), and wherein said second empty liposome (b) consists of sphingomyelin.

In a preferred embodiment, said first empty liposome (a) consists of cholesterol and sphingomyelin, and wherein the amount of cholesterol of said empty liposome (a) is 45%-55% (weight per weight), and wherein preferably the amount of cholesterol of said empty liposome (a) is about 50% (weight per weight), and wherein said first empty liposome (a) comprises said cholesterol and said sphingomyelin as sole lipid components, and wherein said second empty liposome (b) consists of sphingomyelin.

In a preferred embodiment, said mixture of empty liposomes comprises at least 20% (weight per weight) of said first (a) and said second (b) empty liposome, and wherein preferably said mixture of empty liposomes comprises at least 30% (weight per weight) of said first (a) and said second (b) empty liposome.

In a preferred embodiment, said mixture of empty liposomes comprises at least 40% (weight per weight) of said first (a) and said second (b) empty liposome.

In a preferred embodiment, said first empty liposome (a) consists of cholesterol and sphingomyelin, and wherein further preferably the amount of cholesterol of said empty liposome (a) is about 50% (weight per weight), and wherein said mixture of empty liposomes comprises at least 40%, preferably at least 45% (weight per weight) of said first (a) and said second (b) empty liposome.

In a preferred embodiment, said first empty liposome (a) consists of a 1:1 (weight per weight—w/w) mixture of said first empty liposomes and said second liposomes, wherein said first empty liposome is composed of a 1:1 weight ratio (1:1 w/w; 35:65 molar ratio) of cholesterol and sphingomyelin, and said second empty liposome is composed exclusively of sphingomyelin.

In a preferred embodiment, said first empty liposome (a) consists of a 1:1 (weight per weight—w/w) mixture of said first empty liposomes and said second liposomes, wherein said first empty liposome is composed of a 1:1 weight ratio (1:1 w/w; 35:65 molar ratio) of cholesterol and sphingomyelin, and said second empty liposome is composed exclusively of sphingomyelin, and wherein said first empty liposome (a) comprises said cholesterol and said sphingomyelin as sole lipid components, and said second empty liposome (b) comprises said sphingomyelin as sole lipid component.

In a preferred embodiment, the mean diameter of said first empty liposome is about 130 nm, and the mean diameter of said second empty liposome is about 90 nm.

In a preferred embodiment, said composition is for use in adjunctive treatment of pneumonia.

In a preferred embodiment, said pneumonia is a Community Acquired Pneumonia (CAP).

In a preferred embodiment, said pneumonia is a Hospitalization Acquired Pneumonia (HAP).

In a preferred embodiment, said pneumonia is a Ventilator-associated pneumonia (VAP).

In a preferred embodiment, said composition is for use in adjunctive treatment of pneumonia, wherein said pneumonia is a severe pneumonia.

In a preferred embodiment, said composition is for use in adjunctive treatment of pneumonia, wherein said pneumonia is a Community Acquired Pneumonia (CAP) in a human patient. In a preferred embodiment, said pneumonia is a severe pneumonia, wherein said severe pneumonia is severe Community Acquired Pneumococcal Pneumonia (sCAPP).

In a preferred embodiment, said composition is for use in adjunctive treatment of pneumonia, wherein said pneumonia is a Hospital Acquired Pneumonia (HAP) in a human patient.

In a preferred embodiment, said composition is for use in adjunctive treatment of pneumonia, wherein said pneumonia is a Ventilator Associated Pneumonia (HAP) in a human patient.

In a preferred embodiment, said composition is for use in adjunctive treatment of pneumonia, wherein said pneumonia is a Community Acquired Pneumococcal Pneumonia (CAPP) in a human patient.

In a preferred embodiment, said severe pneumonia is a severe Community Acquired Pneumonia (sCAP), and wherein preferably said severe pneumonia is severe Community Acquired Pneumococcal Pneumonia (sCAPP) in a human patient.

In a preferred embodiment, said pneumonia is caused by *Streptococcus pneumoniae, Staphylococcus aureus, Pseudomonas aeruginosa, Enterococcus faecium, Legionella pneumophilia, Haemophilus influenzae, Klebsiella pneumoniae, Escherichia coli, Acinetobacter baumanii, Bordetella pertussis, Serratia marcescens, Stenotrophomonas maltophilia, Moraxella catarrhalis,* or *Mycobacterium tuberculosis.*

In a preferred embodiment, said pneumonia is a severe pneumonia caused by *Streptococcus pneumoniae, Staphylococcus aureus, Pseudomonas aeruginosa, Enterococcus faecium, Legionella pneumophilia, Haemophilus influenzae, Klebsiella pneumoniae, Escherichia coli, Acinetobacter baumanii, Bordetella pertussis, Serratia marcescens, Stenotrophomonas maltophilia, Moraxella catarrhalis,* or *Mycobacterium tuberculosis.*

In a preferred embodiment, said pneumonia, preferably said severe pneumonia is caused by *Streptococcus pneumoniae, Staphylococcus aureus, Pseudomonas aeruginosa, Enterococcus faecium, Haemophilus influenzae, Klebsiella pneumoniae, Escherichia coli, Acinetobacter baumanii, Bordetella pertussis, Moraxella catarrhalis,* or *Mycobacterium tuberculosis.*

In a preferred embodiment, said pneumonia, preferably said severe pneumonia is caused by *Streptococcus pneumoniae, Staphylococcus aureus, Pseudomonas aeruginosa, Enterococcus faecium, Haemophilus influenzae, Klebsiella pneumoniae, Escherichia coli, Acinetobacter baumanii, Bordetella pertussis, Moraxella catarrhalis,* or *Mycobacterium tuberculosis.*

In a preferred embodiment, said pneumonia is caused by *Streptococcus pneumoniae, Staphylococcus aureus, Klebsiella pneumoniae* or *Pseudomonas aeruginosa.*

In a preferred embodiment, said pneumonia, preferably said severe Pneumonia is caused by *Streptococcus pneumoniae, Staphylococcus aureus, Klebsiella pneumoniae, Pseudomonas aeruginosa*.

In a preferred embodiment, said pneumonia is caused by *Streptococcus pneumoniae*.

In a preferred embodiment, said pneumonia is a severe pneumonia caused by *Streptococcus pneumoniae*.

In a preferred embodiment, said pneumonia, preferably said severe pneumonia is a severe Community Acquired Pneumonia (sCAP) caused by *Streptococcus pneumoniae, Staphylococcus aureus, Pseudomonas aeruginosa, Enterococcus faecium, Haemophilus influenzae, Klebsiella pneumoniae, Escherichia coli, Acinetobacter baumanii, Bordetella pertussis, Moraxella catarrhalis*, or *Mycobacterium tuberculosis*, and wherein preferably said sCAP is caused by *Streptococcus pneumoniae, Staphylococcus aureus* or *Pseudomonas aeruginosa*, and wherein further preferably said sCAP is caused by *Streptococcus pneumoniae*.

In a preferred embodiment, said pneumonia preferably said severe pneumonia is a Hospital Acquired Pneumonia (HAP) caused by *Streptococcus pneumoniae, Staphylococcus aureus, Pseudomonas aeruginosa, Serratia marcescens, Haemophilus influenzae, Klebsiella pneumoniae, Escherichia coli, Enterococcus faecium, Acinetobacter baumanii, Bordetella pertussis, Moraxella catarrhalis*, or *Mycobacterium tuberculosis*, and wherein preferably said HAP is caused by *Escherichia coli, Staphylococcus aureus, Klebsiella pneumoniae* or *Pseudomonas aeruginosa*.

In a preferred embodiment, said pneumonia, preferably said severe pneumonia is a Hospital Acquired Pneumonia (HAP) caused by *Streptococcus pneumoniae, Staphylococcus aureus, Pseudomonas aeruginosa, Serratia marcescens, Haemophilus influenzae, Klebsiella pneumoniae, Escherichia coli, Enterococcus faecium, Acinetobacter baumanii, Bordetella pertussis, Moraxella catarrhalis*, or *Mycobacterium tuberculosis*, and wherein preferably said HAP is caused by *Escherichia coli, Staphylococcus aureus, Klebsiella pneumoniae* or *Pseudomonas aeruginosa*.

In a preferred embodiment, said pneumonia, preferably said severe pneumonia is a severe Community Acquired Pneumonia (sCAP), wherein said severe Community Acquired Pneumonia (sCAP) is a severe Community Acquired Bacterial Pneumonia, preferably a severe Community Acquired Pneumococcal Pneumonia (sCAPP) in a human patient, and wherein further preferably said sCAPP is a sCAPP caused by *Streptococcus pneumoniae*.

In a preferred embodiment, said pneumonia, preferably said severe pneumonia is caused by a bacterial infection, wherein said bacterial infection is an infection caused by *Streptococcus pneumoniae, Staphylococcus aureus, Pseudomonas aeruginosa, Haemophilus influenzae, Klebsiella pneumoniae, Escherichia coli, Acinetobacter baumanii, Bordetella pertussis, Moraxella catarrhalis*, or *Mycobacterium tuberculosis*, and wherein preferably said bacterial infection is an infection caused by *Streptococcus pneumoniae, Staphylococcus aureus* or *Pseudomonas aeruginosa*, and wherein further preferably said bacterial infection is an infection caused by *Streptococcus pneumoniae*.

In a preferred embodiment, said pneumonia, preferably said severe pneumonia is a severe Community Acquired Pneumonia (sCAP) caused by a bacterial infection, wherein said bacterial infection is an infection caused by *Streptococcus pneumoniae, Staphylococcus aureus, Pseudomonas aeruginosa, Haemophilus influenzae, Klebsiella pneumoniae, Escherichia coli, Acinetobacter baumanii, Bordetella pertussis, Moraxella catarrhalis*, or *Mycobacterium tuberculosis*, and wherein preferably said bacterial infection is an infection caused by *Streptococcus pneumoniae, Staphylococcus aureus* or *Pseudomonas aeruginosa*, and wherein further preferably said bacterial infection is an infection caused by *Streptococcus pneumoniae*.

In a preferred embodiment, said pneumonia, preferably said severe pneumonia is a severe Community Acquired Pneumonia (sCAP), and wherein said sCAP is a sCAP caused by a bacterial infection, wherein said bacterial infection is a pneumococcal infection, and wherein said pneumococcal infection is an infection caused by *Streptococcus pneumoniae*.

In a preferred embodiment, said treatment is adjunctive to antibiotic therapy, preferably to standard antibiotic therapy.

In a preferred embodiment, said antibiotic therapy, preferably of said standard antibiotic therapy, is selected from ceftriaxone, spiramycin, amoxicillin, amoxicillin/clavulanic acid, gentamicin, piperacilin/tazobactam, cefuroxime, penicillin, azithromycin, clarithromycin, erythromycin, doxycycline, cefotaxime, ampicillin, Ertapenem, cefepime, imipenem, meropenem, ciprofloxacin, levofloxacin, vancomycin, linezolid, moxifloxacin and gemifloxacin, and wherein preferably said antibiotic of said antibiotic therapy, preferably of said standard antibiotic therapy, is selected from ceftriaxone, spiramycin, amoxicillin, gentamicin, levofloxacine, piperacilin/tazobactam, amoxicillin/clavulanic acid, cefuroxime, and penicillin.

In a preferred embodiment, said antibiotic therapy, preferably standard antibiotic therapy, is an intraveneous (IV) or an oral antibiotic therapy, preferably standard intraveneous (IV) or oral antibiotic therapy.

In a preferred embodiment, said composition is in the form of a solution for intravenous administration, preferably intravenous infusion, comprising between 10 and 40 gram of said mixture of empty liposomes per liter solution, preferably between 10 and 20 gram of said mixture of empty liposomes per liter solution.

In a preferred embodiment, the infusion time of said intravenous administration is up to 3 hours, and wherein preferably the infusion time of said intravenous administration is 10 minutes to 2 hours.

In a preferred embodiment, said composition is administered in at least 2 doses. In a preferred embodiment, said composition is administered in at least 2 doses, in a first dose and in a second dose, and wherein the interval between said first dose and said second dose is 6 to 96 hours, preferably 12 to 72 hours, further preferably 24 to 48 hours and again further preferably 24 or 48 hours.

In a preferred embodiment, said composition is administered in 2 to 4 doses, preferably in two doses, over 12 to 72 hours, further preferably in two doses over 24 to 48 hours, preferably with an interval of 24 or 48 hours.

In a preferred embodiment, said composition is administered in at least 2 doses to said human patient, in a first dose and in a second dose, and wherein the interval between said first dose and said second dose is 20 to 28 hours, preferably 24 hours.

In a preferred embodiment, each of said dose is 1 mg/kg to 64 mg/kg, preferably 2 mg/kg to 32 mg/kg, further preferably 3 to 25 mg/kg, again further preferably 4 mg/kg to 16 mg/mg.

In a preferred embodiment, each of said dose is 2 mg/kg to 8 mg/kg, preferably 2 mg/kg to 6 mg/kg, further preferably 3 to 5 mg/kg, again further preferably 4 mg/kg.

In a preferred embodiment, each of said dose is 10 mg/kg to 22/kg, preferably 12 mg/kg to 20/kg, further preferably 14 mg/kg to 18/kg, again further preferably 16 mg/kg.

In a preferred embodiment, said composition is administered in the form of a solution for intravenous administration.

In a preferred embodiment, said composition is administered to said human patient in, preferably at least, 2 doses, in a first dose and in a second dose, wherein an interval of 20 to 48 hours, preferably of 24 hours is between said administration of said first dose and said administration of said second dose, and wherein said composition is in the form of a solution for intravenous administration.

In a preferred embodiment, said composition is administered in at least 2 doses, wherein a first dose is administered no more than 12 h after diagnosis of said pneumonia, preferably of said CAP or sCAP, and further preferably of said sCAPP.

In a preferred embodiment, said composition is administered in at least 2 doses, wherein a first dose is administered no more than 24 h after start of said antibiotic therapy, preferably IV antibiotic therapy.

In a preferred embodiment, said composition is administered in at least 2 doses, wherein a first dose is administered no more than 60 h after start of said oral antibiotic therapy.

In a preferred embodiment, said pneumonia requires stay at the hospital, preferably at the intensive care unit (ICU) in a hospital.

In a preferred embodiment, said severe pneumonia, further preferably said sCAP, requires stay at the hospital.

In a preferred embodiment, said pneumonia, preferably said severe pneumonia, further preferably said sCAP, requires stay at the intensive care unit (ICU), preferably at the intensive care unit (ICU) in a hospital.

In a preferred embodiment, said pneumonia, preferably said severe pneumonia, further preferably said sCAP, requires stay of said patient at a hospital, and wherein said treatment is adjunctive to antibiotic therapy, preferably to standard antibiotic therapy, and wherein said adjunctive treatment reduces the duration of stay at said hospital as compared to a stay at the hospital when no such treatment is effected.

In a preferred embodiment, the reduction of duration of stay at the hospital due to said adjunctive treatment is at least one day, preferably two days, further preferably three days, again further preferably four days, again further preferably five days, again further preferably six days, again further preferably seven days, again further preferably eight days, again further preferably nine days.

In a preferred embodiment, wherein the duration of stay at the hospital is at most two weeks.

In a preferred embodiment, said pneumonia, preferably said severe pneumonia, further preferably said sCAP, requires stay at the intensive care unit (ICU), and wherein said treatment is adjunctive to antibiotic therapy, preferably to standard antibiotic therapy, and wherein said adjunctive treatment reduces the duration of stay at the intensive care unit (ICU) as compared to a stay at the intensive care unit (ICU) when no such treatment is effected.

In a preferred embodiment, the reduction of duration of stay at the intensive care unit (ICU) is at least one day, preferably two days, further preferably three days, again further preferably four days, again further preferably five days, again further preferably six days, again further preferably seven days.

In a preferred embodiment, the duration of stay at the intensive care unit (ICU) is at most one week.

In a preferred embodiment, said pneumonia, preferably said severe pneumonia, further preferably said sCAP, is cured in less time as compared when no such adjunctive treatment, preferably when no such treatment adjunctive to said antibiotic therapy, preferably to said standard antibiotic therapy, is effected.

In a preferred embodiment, said cure in less time is at least one day less in time, preferably two days less in time or further preferably at least three days less in time.

In a preferred embodiment, said cure in less time is represented by normalization of organ function at least one day less in time, preferably two days less in time or further preferably at least three days less in time as compared when no such adjunctive treatment, preferably when no such treatment adjunctive to said antibiotic therapy, preferably to said standard antibiotic therapy, is effected.

In a preferred embodiment, said cure in less time is represented by normalization of blood inflammatory markers, preferably of CRP and/or PCT and/or IL-6, at least one day less in time, preferably two days less in time or further preferably at least three days less in time as compared when no such adjunctive treatment, preferably when no such treatment adjunctive to said antibiotic therapy, preferably to said standard antibiotic therapy, is effected.

In a preferred embodiment, said cure in less time is represented by normalization of organ function and of blood inflammatory markers, preferably of CRP and/or PCT and/or IL-6, at least one day less in time, preferably two days less in time or further preferably at least three days less in time as compared when no such adjunctive treatment, preferably when no such treatment adjunctive to said antibiotic therapy, preferably to said standard antibiotic therapy, is effected.

In a preferred embodiment, said cure in less time is represented by a decrease of the SOFA score, at least one day less in time, preferably two days less in time or further preferably at least three days less in time as compared when no such adjunctive treatment, preferably when no such treatment adjunctive to said antibiotic therapy, preferably to said standard antibiotic therapy, is effected.

In a preferred embodiment, said cure in less time is represented by a decrease of the APACHE II score, at least one day less in time, preferably two days less in time or further preferably at least three days less in time as compared when no such adjunctive treatment, preferably when no such treatment adjunctive to said antibiotic therapy, preferably to said standard antibiotic therapy, is effected.

In a preferred embodiment, said cure in less time is represented by a decrease of the APACHE II score and the SOFA score, at least one day less in time, preferably two days less in time or further preferably at least three days less in time as compared when no such adjunctive treatment, preferably when no such treatment adjunctive to said antibiotic therapy, preferably to said standard antibiotic therapy, is effected.

In a preferred embodiment, said treatment of said pneumonia, preferably said severe pneumonia, further preferably said sCAP, again further preferably said sCAPP, reduces the SOFA score of said patient of at least 40% after 8 days of the first dose with said composition, preferably after 7 days of the first dose with said composition, further preferably after 6 days of the first dose with said composition, and again further preferably after 5 days of the first dose with said composition.

In a preferred embodiment, said treatment of said pneumonia, preferably said severe pneumonia, further preferably said sCAP, again further preferably said sCAPP, reduces the APACHE II score of said patient of at least 20% after 8 days of the first dose with said composition, preferably after 6 days of the first dose with said composition, further preferably after 5 days of the first dose with said composition, and again further preferably after 4 days of the first dose with said composition.

EXAMPLES

Liposomes:

Sphingomyelin (CAS No. 85187-10-6) from egg yolk was purchased from Sigma (S0756), Avanti Polar Lipids (860061) or Lipoid GmbH. Cholesterol (CAS No. 57-88-5) from ovine wool grease was purchased from Sigma (C-8667), Avanti Polar Lipids (70000) or Dishman Netherlands B. V. It is in accordance with the present invention that sphingomyelin and cholesterol comprised by or consisted of by the inventive mixtures of empty liposomes may be either obtained from natural sources as indicated above or alternatively by way of chemical synthesis.

Liposomes Preparation:

Unilamellar sphingomyelin:cholesterol (35:65 molar ratio) and sphingomyelin only (100%) liposomes were prepared using sonication or microfluidization (e.g. high pressure homogenization or according to a hydration, extrusion, and diafiltration process protocol.

Sonication:

The lipids were individually dissolved in chloroform at 1 mg/ml concentrations and stored at −20° C. For the preparation of liposomes the chloroform solutions of individual lipids were mixed in the proportions, as required, to produce routinely 50-500 μl of the final solution. Chloroform was completely evaporated for 20-50 min at 60° C. 50 μl or 100 μl of Tyrode's buffer (140 mM NaCl, 5 mM KCl, 1 mM $MgCl_2$, 10 mM glucose, 10 mM HEPES; pH=7.4) containing 2.5 mM $CaCl_2$ was added to the tubes containing films of dried lipids and vigorously vortexed. The lipid suspensions were incubated for 20-30 min at 45° C. in an Eppendorf thermomixer with vigorous shaking. To produce liposomes, the final lipid suspensions were sonicated 3×5 sec at 6° C. in a Bandelin Sonopuls sonicator at 70% power. The liposomal preparations were left for at least 1 hour at 6° C. before they were used in experiments.

Hydration, Extrusion, and Diafiltration Process Protocol:

In an alternative method, each liposomal formulation was made by the ethanol hydration and extrusion method. Lipids were individually dissolved in ethanol and t-butanol while mixing at elevated temperature (~55° C.). The lipid solution was then added to a PBS Buffer Solution (Sodium Chloride, Monosodium Phosphate, Dihydrate and Disodium Phosphate, Dihydrate dissolved in water for injection while mixing, adjusted to a pH of 7.0-7.4 with either hydrochloric acid (HCl) or sodium hydroxide (NaOH) as required, and filtered through a 0.2 μm filter) while mixing at elevated temperature (~65° C.) for approximately 30 minutes. The ensuing process fluid was then extruded repeatedly through a series of polycarbonate track-etched membranes at elevated pressure and temperature (~65° C.) until the desired particle size was achieved, as measured by dynamic light scattering (example of extruder: LIPEX® Extruders). The ensuing process fluid was then concentrated approximately 2-fold using a 100,000 molecular weight cut-off hollow-fiber cartridge and then diafiltered against approximately 10 volume exchanges of the PBS Buffer Solution to remove the ethanol and t-butanol. At the end of diafiltration, the process fluid was concentrated by approximately 30% to allow subsequent dilution to target lipid concentration. Before dilution, the process fluid was filtered through a 0.2 μm sterilizing-grade filter in order to remove any larger liposomes which could clog the filter during Sterile Filtration. The process fluid was then diluted to a target of 40 mg/mL total lipid with the PBS Buffer Solution. The final formulations were aseptically filtered through two 0.2 μm sterilizing grade filters in series and aseptically filled into glass tubing vials.

The concentration of individual lipids in the liposomes is always given as the weight per weight ratio. In liposomes containing sphingomyelin and cholesterol, the 1:1 (weight per weight) ratio corresponds to 50% (weight per weight) or to 35:65 molar ratio. Specifications are described in Table 1.

TABLE 1

| Specifications liposomes | | | | |
|---|---|---|---|---|
| Mean diameter (nm) | Polydispersity index | Zeta potential (mV) | Osmolality (mmol/kg) | pH |
| 40 to 400 | <0.45 | −25 to +2 | 250-400 | 6.5-8.0 |

CURB-65 Score:

CURB-65, also known as the CURB criteria, is a clinical prediction rule well-known to the skilled person in the art that has been validated for predicting mortality in community-acquired pneumonia (Lim W S, et al. (2003) *Thorax* 58(5): 377-82). The CURB-65 is recommended by the British Thoracic Society for the assessment of severity of pneumonia (British Thoracic Society Standards of Care Committee (2001). "BTS Guidelines for the Management of Community Acquired Pneumonia in Adults". *Thorax*. 56. Suppl 4: IV1-64)

The score is an acronym for each of the risk factors measured. Each risk factor scores one point, for a maximum score of 5:

Confusion of new onset (defined as an AMTS of 8 or less)
Blood Urea nitrogen greater than 7 mmol/l (19 mg/dL)
Respiratory rate of 30 breaths per minute or greater
Blood pressure less than 90 mmHg systolic or diastolic blood pressure 60 mmHg or less
Age 65 or older.

APACHE II:

The APACHE II is an acronym for Acute Physiology and Chronic Health Evaluation and is calculated according to Table 2 (Knaus W A et al. APACHE II: a severity of disease classification system. *Crit Care Med.* 1985 October; 13(10): 818-29):

TABLE 2

| APACHE II Score | |
|---|---|
| | POINTS |
| Age | |
| under 45 | 0 |
| 45-54 | 2 |
| 55-64 | 3 |
| 65-74 | 5 |
| over 74 | 6 |
| History of severe organ insufficiency or immunocompromised | |
| Yes, and non-operative or emergency post-operative patient | 5 |
| Yes, and elective post-operative patient | 2 |
| No | 0 |
| Temperature ° C. | |
| over 40.9 | 4 |
| 39-40.9 | 3 |

TABLE 2-continued

APACHE II Score

| | POINTS |
|---|---|
| 38.5-38.9 | 1 |
| 36-38.4 | 0 |
| 34-35.9 | 1 |
| 32-33.9 | 2 |
| 30-31.9 | 3 |
| below 30 | 4 |
| Mean arterial pressure (mm Hg) | |
| over 159 | 4 |
| 130-159 | 3 |
| 110-129 | 2 |
| 70-109 | 0 |
| 50-69 | 2 |
| below 50 | 4 |
| Heart rate (ventricular response) | |
| over 179 | 4 |
| 140-179 | 3 |
| 110-139 | 2 |
| 70-109 | 0 |
| 55-69 | 2 |
| 40-54 | 3 |
| below 40 | 4 |
| Respiratory Rate (non-ventilated or ventilated | |
| over 49 | 4 |
| 35-49 | 3 |
| 25-34 | 1 |
| 12-24 | 0 |
| 10-11 | 1 |
| 6-9 | 2 |
| below 6 | 4 |
| Oxygenation (use PaO2 if FiO2 < 50%, otherwise A-a | |
| A-a gradient over 499 | 4 |
| A-a gradient 350-499 | 3 |
| A-a gradient 200-349 | 2 |
| A-a below 200 (if FiO2 over 49%) or pO2 more than 70 (if | 0 |
| pO2 = 61-70 | 1 |
| pO2 = 55-60 | 3 |
| pO2 below 55 | 4 |
| Arterial pH | |
| over 7.69 | 4 |
| 7.60-7.69 | 3 |
| 7.50-7.59 | 1 |
| 7.33-7.49 | 0 |
| 7.25-7.32 | 2 |
| 7.15-7.24 | 3 |
| below 7.15 | 4 |
| Serum sodium (mmol/L) | |
| over 179 | 4 |
| 160-179 | 3 |
| 155-159 | 2 |
| 150-154 | 1 |
| 130-149 | 0 |
| 120-129 | 2 |
| 111-119 | 3 |
| below 111 | 4 |
| Serum potassium (mmol/L) | |
| over 6.9 | 4 |
| 6-6.9 | 3 |
| 5.5-5.9 | 1 |
| 3.5-5.4 | 0 |
| 3-3.4 | 1 |
| 2.5-2.9 | 2 |
| below 2.5 | 4 |
| Serum creatinine (mg/dL) | |
| over 3.4 and ACUTE renal failure | 8 |
| 2.0-3.4 and ACUTE renal failure | 6 |
| over 3.4 and chronic | 4 |
| 1.5-1.9 and ACUTE renal failure | 4 |
| 2.0-3.4 and chronic | 3 |
| 1.5-1.9 | 2 |
| 0.6-1.4 | 0 |
| below 0.6 | 2 |
| Hematocrit (%) | |
| over 59.9 | 4 |
| 50-59.9 | 2 |
| 46-49.9 | 1 |
| 30-45.9 | 0 |
| 20-29.9 | 2 |
| below 20 | 4 |
| White blood count (total/cubic mm in 1000's) | |
| over 39.9 | 4 |
| 20-39.9 | 2 |
| 15-19.9 | 1 |
| 3.0-14.9 | 0 |
| 1.0-2.9 | 2 |
| below 1.0 | 4 |
| Glasgow Coma scale | |
| Eyes open | |
| Spontaneous | 4 |
| To speech | 3 |
| To pain | 2 |
| Absent | 1 |
| Verbal | |
| Converses/Oriented | 5 |
| Converses/Disoriented | 4 |
| Inappropriate | 3 |
| Incomprehensible | 2 |
| Absent | 1 |
| Motor | |
| Obeys | 6 |
| Localises pain | 5 |
| Withdraws (flexion) | 4 |
| Decorticate (flexion) rigidity | 3 |
| Decerebrate (flexion) rigidity | 2 |
| Absent | 1 |
| Score relative to GCS: 15 − (minus) Actual GCS | |

The APACHE II Score aims at providing an approximate of the chances of mortality of a patient or a group of patients based on the total score obtained. The mortality interpretation of the score is described in Table 3:

TABLE 3

Apache II Score/Approximate Mortality Interpretation

| Total points range | Chance of mortality if patient had no operation | Chance of mortality in post-operative situation |
|---|---|---|
| 0-4 | 4% | 1% |
| 5-9 | 8% | 3% |
| 10-14 | 15% | 7% |
| 15-19 | 24% | 12% |
| 20-24 | 40% | 30% |
| 25-29 | 55% | 35% |
| 30-34 | 73% | 73% |
| 35-100 | 85% | 88% |

SOFA:

The SOFA score is an acronym for Sequential Organ Failure Assessment and is calculated according to Table 4 (S. Vosylius, J. Sipylaite and J. Ivaskevicius, *Croat Med J*, 45 (2004), 715-20):

TABLE 4

SOFA Score

| Variables | Score | | | | |
|---|---|---|---|---|---|
| | 0 | 1 | 2 | 3 | 4 |
| Respiration: PaO2/FiO2 | >400 | 301-400 | 201-300 | 101-200* | ≤100* |
| Coagulation: platelets, 10³/µl | >150 | 101-150 | 51-100 | 21-50 | ≤20 |
| Liver: bilirubin, µmol/L | <20 | 20-32 | 33-101 | 102-204 | >204 |
| Cardiovascular: hypotension | No hypotension | MAP** <70 mm Hg | Dopamine ≤5, or dobutamine (any dose)*** | Dopamine >5, or epinephrine ≤0.1, or norepinephrine ≤0.1** | Dopamine >15, or epinephrine >0.1, or norepinephrine >0.1*** |
| Central Nervous system: Glasgow Coma Score**** | 15 | 13-14 | 10-12 | 6-9 | <6 |
| Renal: Creatinine µmol/L | <110 | 110-170 | 171-299 | 300-440 | <440 |

*With respiratory support
**MAP—mean arterial pressure
***Adrenergic agents administered for at least 1 h (dosages are in µg/kg/min)
****As defined in the APACHE II Score above

EXAMPLE 1

Treatment of Patients with Severe Community-Acquired Pneumonia Caused by *Streptococcus Pneumoniae*

In the study reported thereafter, a very preferred mixture of empty liposomes of the present invention, named CAL02, is administered intravenously (IV) as adjunctive treatment in addition to standard antibiotic therapy, in patients with severe community-acquired pneumonia (CAP) due to *Streptococcus pneumoniae* requiring management at the intensive care unit (ICU). Said very preferred inventive mixture of empty liposomes (CAL02) consists of a 1:1 (weight per weight—w/w) mixture of said first empty liposomes and said second liposomes, wherein said first empty liposome is composed of a 1:1 weight ratio (1:1 w/w; 35:65 molar ratio) of sphingomyelin and cholesterol, and said second empty liposomes is composed exclusively of sphingomyelin.

All 19 patients (male and female) of this study received standard-of-care antibiotic therapy according to standard practice (Mandell et al, IDSA/ATS Guidelines for CAP in Adults, CID 2007:44 (Suppl 2), S27-S72), plus CAL02 or Placebo (physiological 0.9% NaCl solution). Two dose levels of CAL02 (4 mg/kg (Low Dose) and 16 mg/kg (High Dose)) were tested.

Each patient received two infusions of CAL02 or placebo (with a 24-hour or 48-hour interval between these administrations), shortly after the diagnosis of severe disease (no more than 12 h after diagnosis of severe CAP or severe Community Acquired Pneumococcal Pneumonia (CAPP) and early on in the antibiotic treatment (no more than 24 h after start of IV antibiotic treatment (or 60 h if oral). Patients were followed up for a total of 29 days.

In the present study, all patients received standard-of-care antibiotic therapy as per local guidelines, with any antibiotics, either alone or in combination. Dose and frequency of administration of said standard of care antibiotic therapy selected by the Investigator followed the labelling of therapies approved in their respective country.

The inclusion criteria for this study were, in particular, as follows:
1. Male or female 18-80 years old, inclusive, with body weight 40-140 kg, inclusive
2. Patient diagnosed with severe CAP, with new pulmonary infiltrate found on a chest X-ray, and newly acquired respiratory symptoms (cough, sputum production) and auscultatory findings of abnormal breath sounds and crackles
3. CURB-65 score≥3 in patients aged≥65 and CURB-65≥2 in patients aged<65
4. CAPP diagnosed as severe pneumonia based on the major OR on the minor severity criteria shown in the following list, and requiring Intensive-Care Unit (ICU) admission (screening may take place at the emergency department).

Major criteria: patient meeting at least one of the two following major severity criteria for CAP:
 i. Receiving invasive mechanical ventilation support
 ii. Receiving treatment with vasopressors at therapeutic doses (i.e. dopamine>5 mg/kg/min or any dose of epinephrine, norepinephrine, phenylephrine or vasopressin) for at least 2 hours to maintain or attempt to maintain systolic blood pressure>90 mm Hg (or mean arterial pressure>70 mm Hg) after adequate fluid resuscitation Minor criteria: patient meeting three or more of the following minor severity criteria for CAP:
 i. Respiratory rate≥30 breaths/min
 ii. PaO2/FiO2 ratio≤250 mm Hg
 iii. Multilobar infiltrates
 iv. Confusion/disorientation (has to be documented prior to the use of sedative or other new psychotropic medication)
 v. Urea>7 mM (>40 mg/dL)
 vi. Leukopenia (white blood cell count<4,000 cells/mm³)
 vii. Thrombocytopenia (platelet count<100,000 cells/mm³)
 viii. Hypothermia (core temperature<36° C.)
 ix. Systolic blood pressure<90 mm Hg or mean arterial pressure<70 mm Hg and received≥40 mL/kg of fluid resuscitation over at least 2 hours Study Results Five patients were randomized to the Placebo arm, 11 to the CAL02 High Dose arm, and 3 to the CAL02 Low Dose arm. One patient from the High Dose arm was deleted before unblinding because of a major eligibility criteria violation. All patients received antibiotic treatment or combination of antibiotics that was considered appropriate for the patient. Overall, ceftriaxone, spiramycin, amoxicillin, gentamicin, levofloxacine, piperacilin/tazobactam, amoxicillin/clavulanic acid, cefuroxime, and penicillin were used in this study population.

At time of treatment, the average APACHE II was 21.3 and SOFA 7.4. Baseline characteristics were homogeneous across arms. However the CAL02 arms proved slightly more severe patients than the Placebo arm, with an APACHE II of 22.1 and 25.3 in the CAL02 High Dose and Low Dose arms, respectively, as compared to 17.4 in the Placebo arm. The three Low Dose patients were all intubated.

Baseline characteristics are summarized in Table 5:

TABLE 5

Patients characteristics at baseline

|  |  | PLACEBO (n = 5) | CAL02 HIGH DOSE (n = 10) | CAL02 LOW DOSE (n = 3) | CAL02 Combined (n = 13) |
|---|---|---|---|---|---|
| Demographic characteristics |  |  |  |  |  |
| Age | Mean | 62.2 | 57.5 | 50.7 | 55.9 |
| BMI | Mean | 29.1 | 25.9 | 20.9 | 24.7 |
| Clinical characteristics |  |  |  |  |  |
| CURB-65 | Mean | 3.2 | 3.5 | 3.3 | 3.5 |
| APACHE II | Mean | 17.4 | 22.1 | 25.3 | 22.8 |
| SOFA | Mean | 7 | 6.5 | 11.0 | 7.5 |
| Mechanical ventilation | n | 2 | 2 | 3 | 5 |
| Bacteremia | n | 0 | 3 | 2 | 5 |
| Severe CAP criteria | Major | 3 | 6 | 3 | 9 |
|  | Minor | 2 | 4 | 0 | 4 |
| Charlson commorbities index | Mean | 2.8 | 3.4 | 5.3 | 3.8 |
| Renal failure | n | 2 | 4 | 2 | 6 |
| Cardiac disorders | n | 3 | 5 | 0 | 5 |
| Thrombocytopenia | n | 1 | 3 | 2 | 5 |
| PaO2/FiO2 ratio | Median | 113 | 141.5 | 73 | 110 |
| CRP | Median | 376 | 276.35 | 314 | 303 |
| Procalcitonin | Median | 7.04 | 16.3 | 20 | 20 |

19 patients were infected by *S. pneumoniae*. One patient in the Low Dose cohort was also infected by *Escherichia coli*. One patient in the Low Dose cohort was also infected by *Klebsiella pneumoniae*. One patient in the High Dose cohort was also infected by *Enterococcus faecium*. And 3 patients (one in the Low Dose and two in the High Dose cohort) were infected by *S. aureus*.

One patient died in each arm, causing mortality rates to be 20% in the Placebo arm, 10% in the CAL02 High Dose arm, and 33% in the CAL02 Low Dose arm.

Test of Cure (TOC) visits were predefined at Day 8 (early TOC) and between Day 15 and 22 and at the end of the study (EOS). Said TOC's are medical visits during which judgement of (clinical) cure, and thus efficacy of the treatment, is assessed.

Clinical cure for the present study corresponded to the time when the patient showed resolution of signs and symptoms of pneumonia, when standard laboratory data is back to normal, when fever has subsided (without antipyretics for at least 24 hours) and when the patient shows improvement or a clean Rx film, making antibiotic treatment unnecessary.

At the TOC visit, clinical cure (or clinical outcome) were assessed as follows:
a) Cure: complete resolution of pneumonia signs and symptoms present at baseline, no new symptoms or complications attributable to the pneumonia.
b) Failure: persistence/progression of baseline signs and symptoms of pneumonia; or baseline radiographic abnormalities after at least 2 days of treatment; or development of new pulmonary or extra-pulmonary clinical findings consistent with active infection, or development of new pulmonary or extrapulmonary infection requiring antimicrobial therapy other than or in addition to the IMP; or death due to pneumonia.
c) Unknown: extenuating circumstances precluding classification to one of the above.

Further, the microbiological outcome were assessed at the TOC visits.

At early Test of Cure (TOC) (pre-defined at Day 8), 20% were cured in the Placebo arm, as compared to 50% in the CAL02 High Dose arm. At TOC (pre-defined between Day 15 and 22), all surviving patients were cured. Median time to cure was of 10 days in the Placebo arm and 8 in the CAL02 High Dose arm (Table 6).

TABLE 6

Outcome

|  | Placebo (n = 5) | CAL02 High Dose (n = 10) |
|---|---|---|
| Mortality (n) | 1 (20%) | 1 (10%) |
| Cured at Early TOC (Day 8) | 1/5 (20%) | 5/10 (50%) |
| Cured at TOC (pre-defined between Day 15 and 22) | 100% | 100% |
| Time to cure - median, in days | 10 | 8 |

Figure 1A:
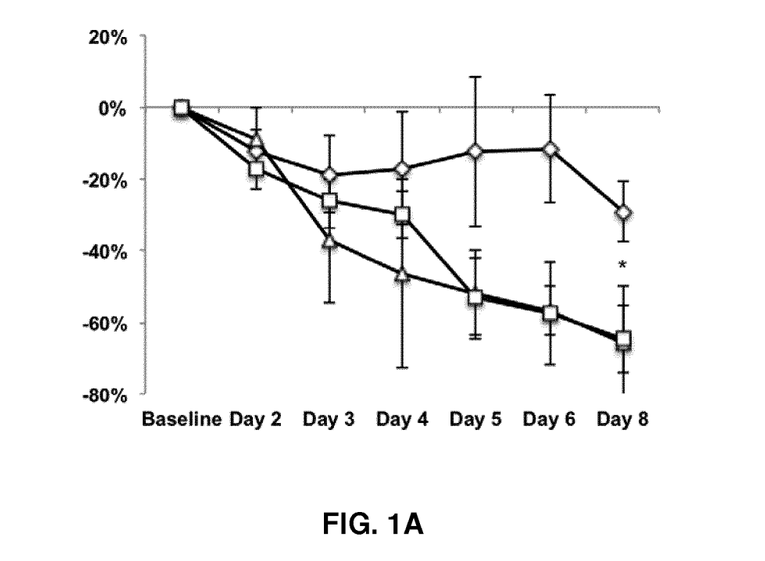
Figure 1B:
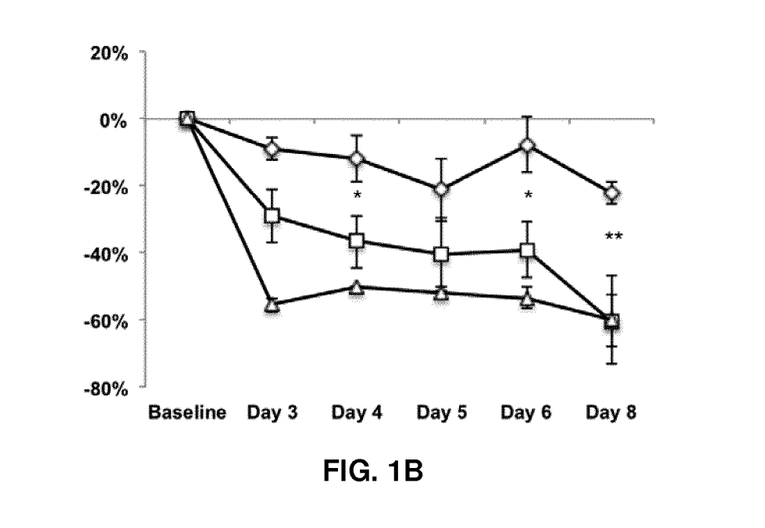

A faster clinical recovery was observed in the CAL02 arms as compared to the Placebo arm: A 50% decrease in the SOFA score was already achieved in 5 days in the CAL02 arms (FIG. 1A). The APACHE II score also decreased more rapidly with CAL02 (High and Low Dose) as compared to Placebo (FIG. 1B).

Figure 2A:
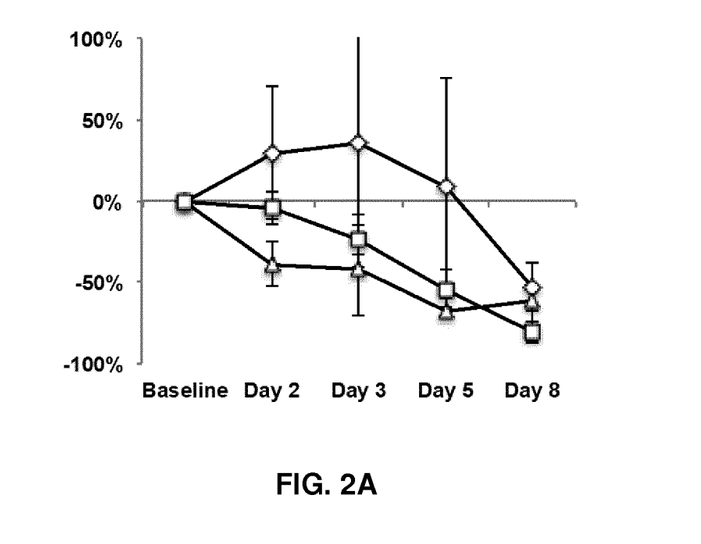
Figure 2B:
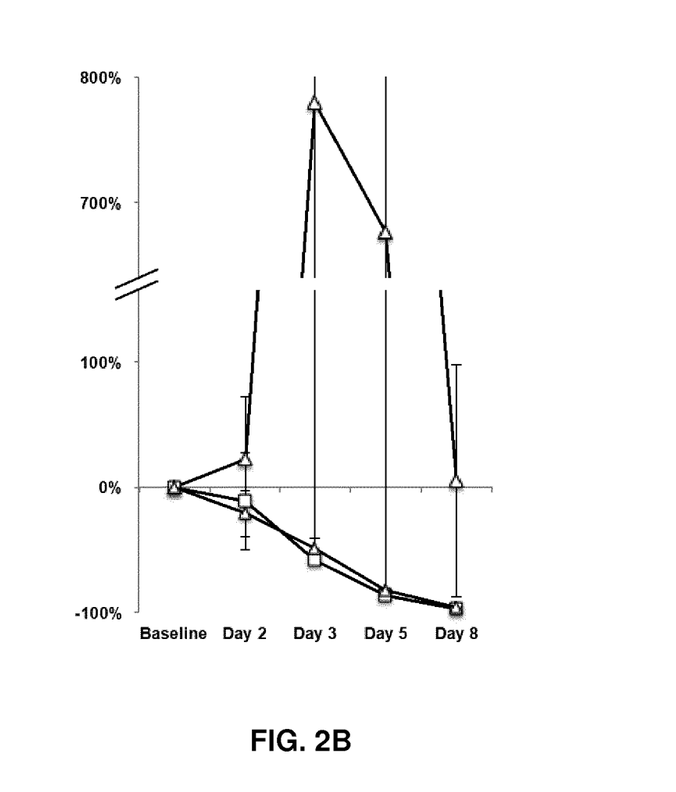
Figure 2C:
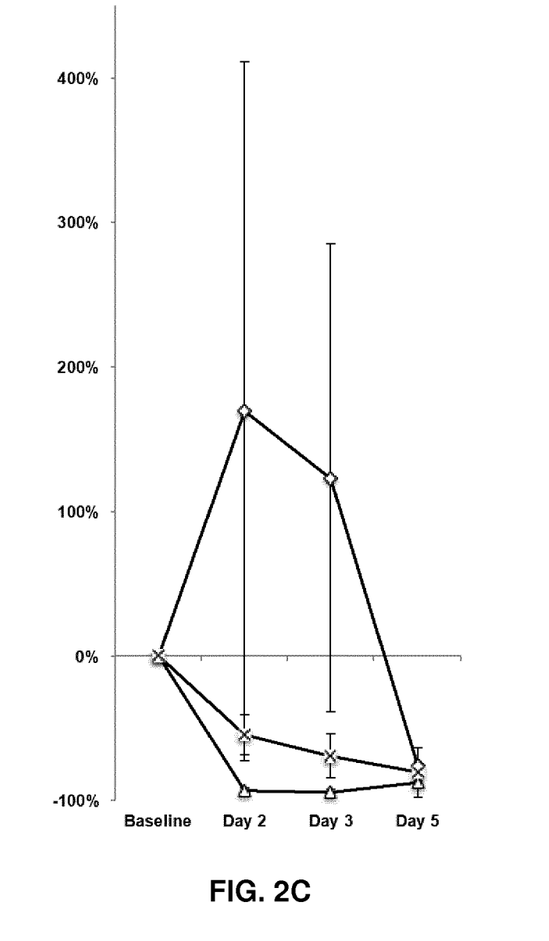

Pharmacodynamic biomarkers (CRP, PCT, IL-6) also returned to normal more quickly with CAL02 (High and Low Dose), as compared to Placebo (FIG. 2).

Figure 3A:
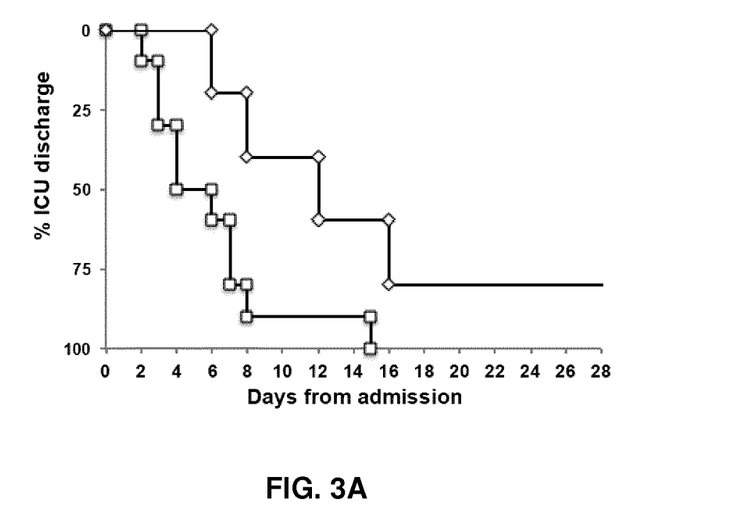
Figure 3B:
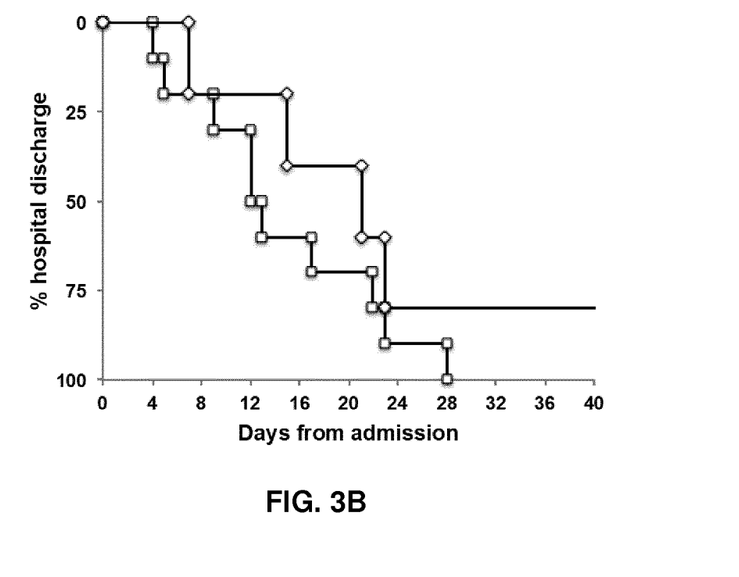

Duration of stay in ICU was significantly reduced, from 12 days in the Placebo arm to 5 days in CAL02 High Dose arm ($p<0.05$) and duration of hospitalization was also reduced, from 21 days in the Placebo arm to 12 and 12.5 days in the CAL02 High Dose and Low Dose arms, respectively (FIG. 3).

The impact of CAL02 treatment was also evaluated on:
- the rate of pneumonia recurrence and/or reinfection
- infiltrates and the resolution of pneumonia, by changes on chest X-rays
- the evolution of arterial blood gases via the PaO2/FiO2 ratio
- the need and the duration of invasive or non-invasive ventilation
- the duration of antibiotic therapy
- the use of concomitant medications and of rescue antibiotics.
- other pharmacodynamic markers such as pancreatic stone protein (PSP)
- vital signs (including include heart rate, systolic and diastolic blood pressure and core body temperature)
- haematology variables (including red blood cell count, haemoglobin and haematocrit, as well as white blood cell count with neutrophils, lymphocytes, monocytes, eosinophils, basophils, and platelet)
- clinical Chemistry variables (including sodium, potassium, CRP, total bilirubin, serum creatinine, glucose, BUN, calcium, inorganic phosphorus, chloride, albumin, alkaline phosphatase, total protein, lactate dehydrogenase (LDH), cholesterol, alanine aminotransferase (ALT=SGPT), aspartate aminotransferase (AST=SGOT), triglycerides and uric acid)
- urinalysis (incuding glucose, protein, bilirubin, urobilinogen and nitrite)
- physical examination (including general appearance, skin, respiratory, cardiovascular, abdominal and nervous system)
- microbiological outcome of the CAP (respiratory, blood and pleural fluid samples) to determine eradication or presumed eradication or persistence or presumed persistence or superinfection or recurrence or new infection or colonisation as stand-alone or as composite endpoints.

Conclusions:

This is the first trial assessing the potential of CAL02, a first-in-class broad-spectrum anti-toxin agent. Safety primary endpoints were met. Despite the fact that CAL02-treated patients were more severe than in the Placebo arm, CAL02-treated patients showed a more rapid clinical improvement. Efficacy trends were consistent across different clinical and biological parameters with both a faster resolution in organ dysfunction and a more rapid decrease in pharmacodynamic biomarkers. These observations are in line with the mechanism of action of CAL02, which aims at protecting against toxin-mediated organ damage and inflammation.

EXAMPLE 2

A randomised, multicentre, double-blind, placebo-controlled, with CAL02, administered intravenously (IV) as adjunctive treatment in addition to standard antibiotic therapy, in patients admitted to the Emergency Room (ER), intermediate care, or intensive care unit (ICU), with a proven or suspected infection requiring (i) intravenous antibiotics and (ii) management at the intensive care unit or intermediate care. Patients receive antibiotic therapy according to standard practice, plus CAL02 or Placebo. Infections include community-acquired pneumonia, hospital-acquired pneumonia, ventilation-associated pneumonia, as well as intra-abdominal infections, skin and soft tissue infections, and urinary tract infections above 70 years old, or bacteraemia.

The invention claimed is:

1. A method of treating severe pneumonia in a human comprising
   administering to said human an antibiotic therapy; and
   intravenously administering to the human at least two, 16 mg/kg doses of a liposomal composition comprising a mixture of empty liposomes,
   wherein said mixture of empty liposomes comprises
     (a) a first empty liposome comprising cholesterol, wherein the amount of cholesterol is at least 30 w/w %; and
     (b) a second empty liposome comprising sphingomyelin
   wherein said pneumonia is cured in less time as compared to a treatment without administration of the liposomal composition.

2. The method of claim 1, wherein the amount of cholesterol of said empty liposome (a) is 45 w/w %-55 w/w %, and wherein said second empty liposome (b) consists of sphingomyelin.

3. The method of claim 1 wherein said first empty liposome (a) consists of cholesterol and sphingomyelin, and wherein the amount of cholesterol of said empty liposome (a) is about 50 w/w %, and wherein said mixture of empty liposomes comprises at least 40 w/w %, of said first empty liposome (a) and said second empty liposome (b).

4. The method of claim 1, wherein said mixture of empty liposomes consists of about a 1:1 w/w mixture of said first empty liposome (a) and said second empty liposome (b),
   wherein said first empty liposome (a) is composed of about a 1:1 w/w; of cholesterol and sphingomyelin, and
   said second empty liposome (b) is composed exclusively of sphingomyelin, and
   wherein said first empty liposome (a) comprises said cholesterol and said sphingomyelin as sole lipid components, and
   said second empty liposome (b) comprises said sphingomyelin as sole lipid component.

5. The method of claim 1, wherein said pneumonia is a Community Acquired Pneumonia.

6. The method of claim 1, wherein said pneumonia is caused by *Streptococcus pneumoniae, Staphylococcus aureus, Pseudomonas aeruginosa, Enterococcus faecium, Legionella pneumophilia, Haemophilus influenzae, Klebsiella pneumoniae, Escherichia coli, Acinetobacter baumanii, Bordetella pertussis, Serratia marcescens, Stenotrophomonas maltophilia, Moraxella catarrhalis*, or *Mycobacterium tuberculosis*.

7. The method composition for use of claim 1, wherein said pneumonia is caused by *Streptococcus pneumoniae*.

8. The method of claim 1, wherein said antibiotic therapy is an intravenous or an oral antibiotic therapy.

9. The method of claim 1, wherein the liposomal composition is administered in a first dose and in a second dose, wherein the interval between said first dose and said second dose is 6 to 96 hours.

10. The method of claim 9, wherein the first dose is administered no more than 24 h after start of said antibiotic therapy.

11. The method of claim 1, wherein said pneumonia requires stay of said patient at a hospital and wherein said method reduces the duration of stay at said hospital as compared to a stay at the hospital without administration of the liposomal composition.

12. The method of claim 11, wherein the reduction of duration of stay at the hospital due to said treatment is at least one day.

13. The method of claim 1, wherein said cure in less time is represented by normalization of organ function at least one day less in time as compared to a treatment without administration of the liposomal composition.

14. The method of claim 1, wherein said cure in less time is represented by normalization of blood inflammatory markers, at least one day less in time as compared to a treatment without administration of the liposomal composition.

15. The method of claim 1, wherein said cure in less time is represented by a decrease of the SOFA score, at least one day less in time as compared to a treatment without administration of the liposomal composition.

16. The method of claim 1, wherein said method reduces the SOFA score of said patient at least 40% 8 days after administration of the liposomal composition.

17. The method of claim 1, wherein said pneumonia is severe Community Acquired Pneumonia (sCAP).

18. The method of claim 1, wherein said pneumonia is severe Community Acquired Bacterial Pneumonia.

19. The method of claim 1, wherein said pneumonia is Community Acquired Pneumococcal Pneumonia.

20. The method of claim 19, wherein said Community Acquired Pneumococcal Pneumonia is severe Community Acquired Pneumococcal Pneumonia.

21. The method of claim 5, wherein said Community Acquired Pneumonia is a severe Community Acquired Pneumonia.

* * * * *